United States Patent [19]
Fleming et al.

[11] Patent Number: 5,871,769
[45] Date of Patent: Feb. 16, 1999

[54] METHODS AND COMPOSITIONS FOR THE PREVENTION AND TREATMENT OF DIABETES MELLITUS

[75] Inventors: Thomas E. Fleming, St. Louis, Mo.; Herbert C. Mansmann, Jr., Newton Square, Pa.

[73] Assignee: Fleming & Company, Pharmaceuticals, Fenton, Mo.

[21] Appl. No.: 844,908

[22] Filed: Apr. 23, 1997

Related U.S. Application Data

[63] Continuation-in-part of Ser. No. 588,564, Jan. 18, 1996.
[51] Int. Cl.$^6$ .............................. A61F 2/02; A61F 9/02; A61F 13/02; A61K 9/48
[52] U.S. Cl. .......................... 424/423; 424/434; 424/435; 424/436; 424/443; 424/451; 424/464
[58] Field of Search .................................. 424/423, 434, 424/435, 436, 443, 451, 464

[56] References Cited

U.S. PATENT DOCUMENTS

| 5,002,780 | 3/1991 | Batka et al. ............................... 426/72 |
| 5,260,279 | 11/1993 | Greenberg . |
| 5,504,072 | 4/1996 | Schmidl et al. . |
| 5,550,166 | 8/1996 | Ostlund et al. . |

OTHER PUBLICATIONS

Mansmann, Jr., H.C., "Consider Magnesium Homeostasis" *Pediatric Asthma, Allergy & Immunology*, 5, pp. 273–279 (1991).
Physicians' Desk Reference, 50th Edition (1996) p. 1005, "Magonate Tablets, Magonate Liquid".
Altura, B.M. and Altura, B.T., 1985, *Magnesium* 4: 226–244.
American Diabetes Association, 1992, *Diabetes Care* 15: 1065–1067.
Bardicef, M. et al., 1995, *Am J. Gynecol.* 172: 1009–1013.
Del Maestro, R. F., 1980., *Acta. Physiol. Scand.* 492 (Suppl.): 153–168.
Deuster, P.A. et al., 1987 *Clin. Chem.* 33: 529–532.
Dietze G., et al., 1979, *Adv. Exper. Med. Biol.* 120A: 511–520.
Elin, R. J., 1987, *Clin Chem.* 33: 1965–1970.
Fantone, J. C., et. al., 1982, *Am. J. Pathol.* 107: 395–418.
Freinkel, N. et al., 1985, *N. Engl. J. Med.* 313: 96.
Fridovich, I., 1983, *Annu. Rev. Pharmacol. Taxicol.* 23: 239–257.
LaPorte, R. E. et al., 1981, *Diabetes* 30: 279.
Mak, I.T., et al., 1990, *Biochem. Pharm.* 40: 2169–2175.
Mak, I.T., et al., 1995, *Biochem. Pharmacol.* 50:1531–1534.
Mak, I.T., et al., 1992, *Cir. Res.* 70: 1099–1103.
Mak, I.T. & Weglicki, W.B., 1994, *Method Enzymol.* 234: 620–630.
Mather, H. M. et al., 1985, *Br. Med. J.* 291: 1081.
McNair, P. et al., 1978, *Diabetes* 27: 1075–1077.
Moles, K.W. and McMullen, J.K, 1982, *Br. Med.J.* 285: 262.
Pao, E. M., Micke, S.J. 1981, *Food Technol.* 35– 58–69.
Rayssiguier, Y. And Gueux, E., 1986, *J. Am. Coll. Nutr.* 5: 507–519.
Resnick, L. M. et al., 1987, *Proc. Natl. Acad. Sci. USA* 84: 7663–7667.
Tribble, D. L. et al. 1987, *Hepatology* 7: 377–386.
Yajnik, C.S. et al., 1984, *Br. Med. J.* 288: 1032–1034.

*Primary Examiner*—Carlos A. Azpuru
*Attorney, Agent, or Firm*—Senniger, Powers, Leavitt & Roedel

[57] ABSTRACT

The present invention relates to methods and compositions for the prevention and/or treatment of diabetes mellitus, using magnesium gluconate alone or in combination with one or more antioxidants or conventional diet and/or insulin therapy. The invention also relates to inhibition of production of oxygen free radicals and lipid peroxidation.

13 Claims, 4 Drawing Sheets

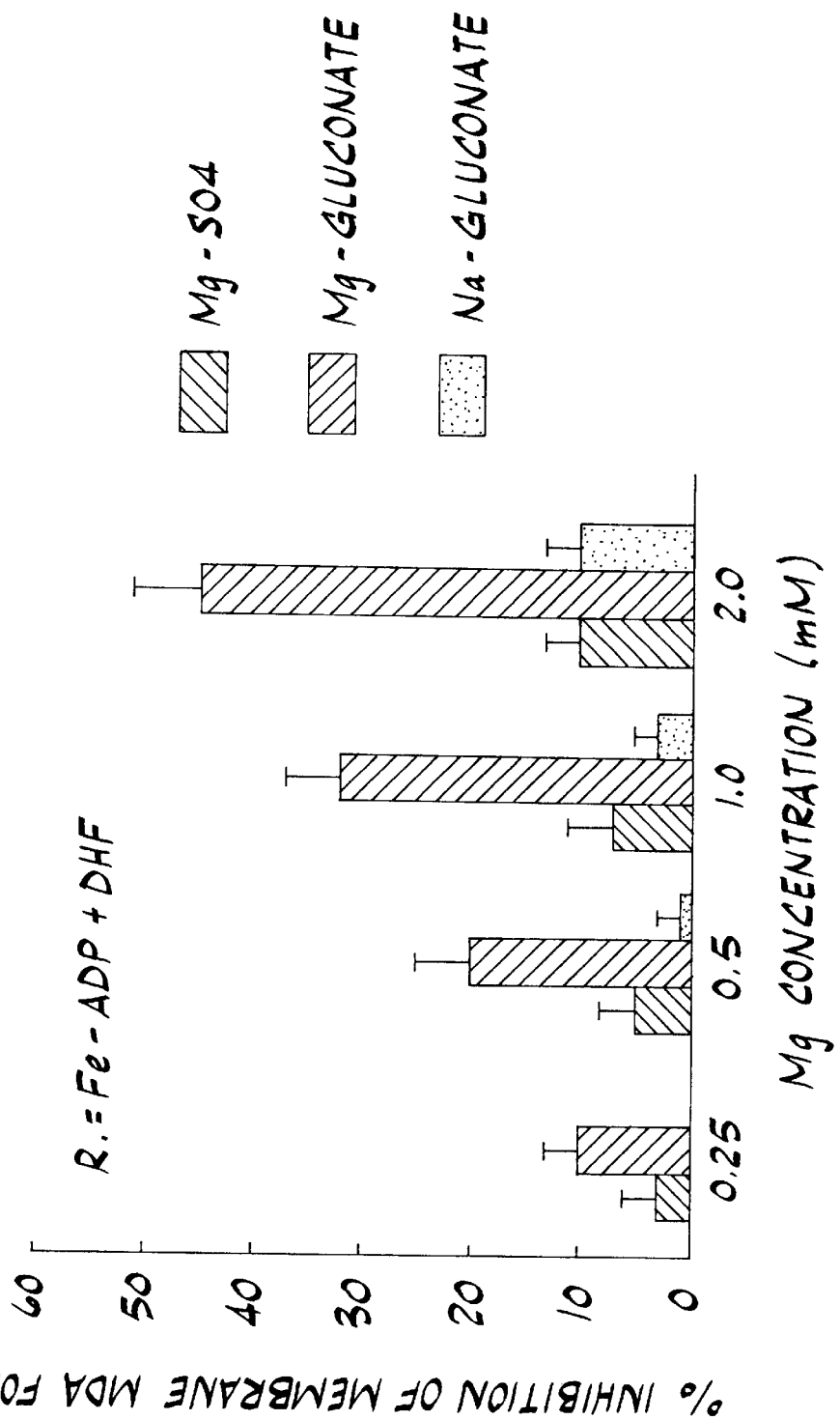

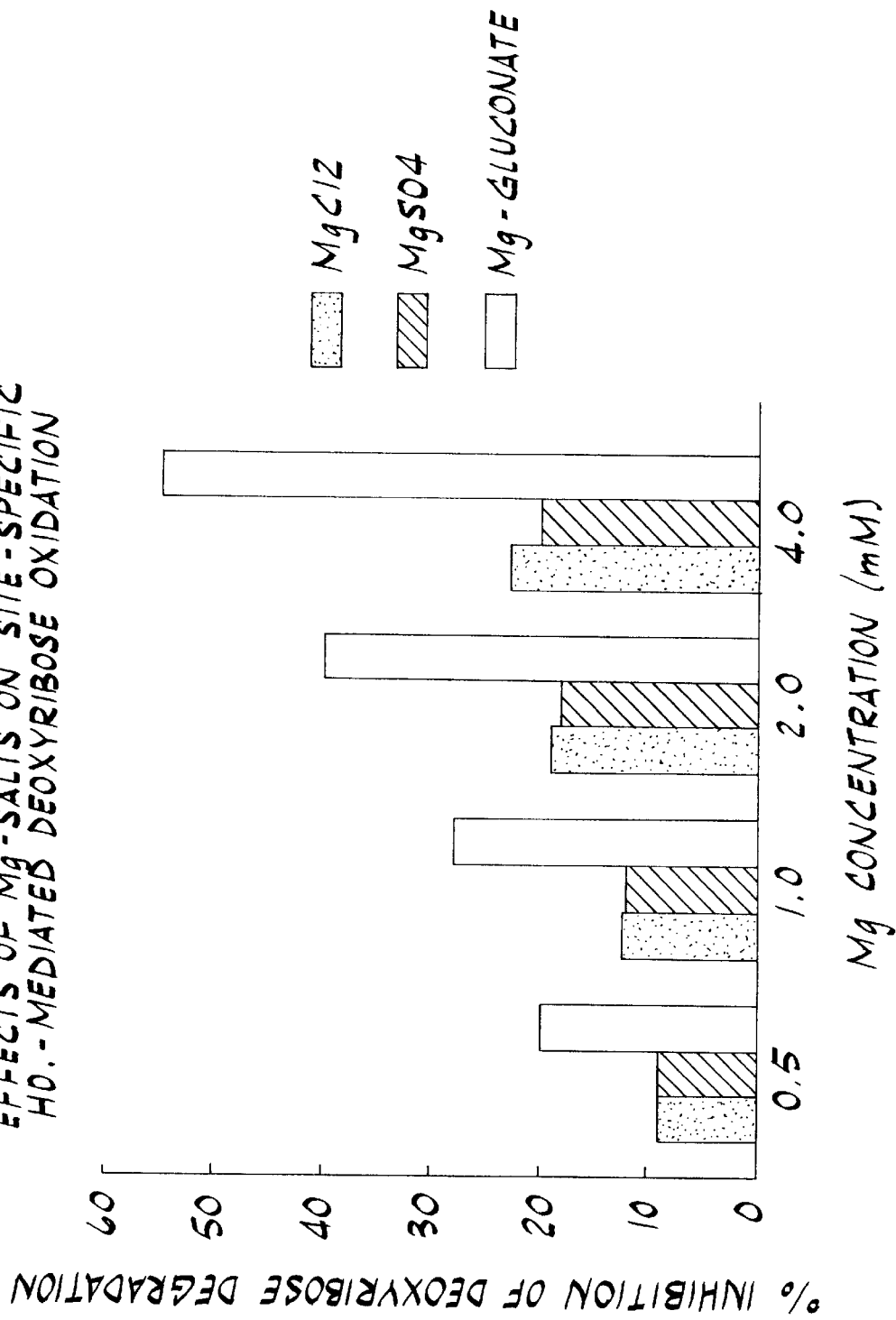

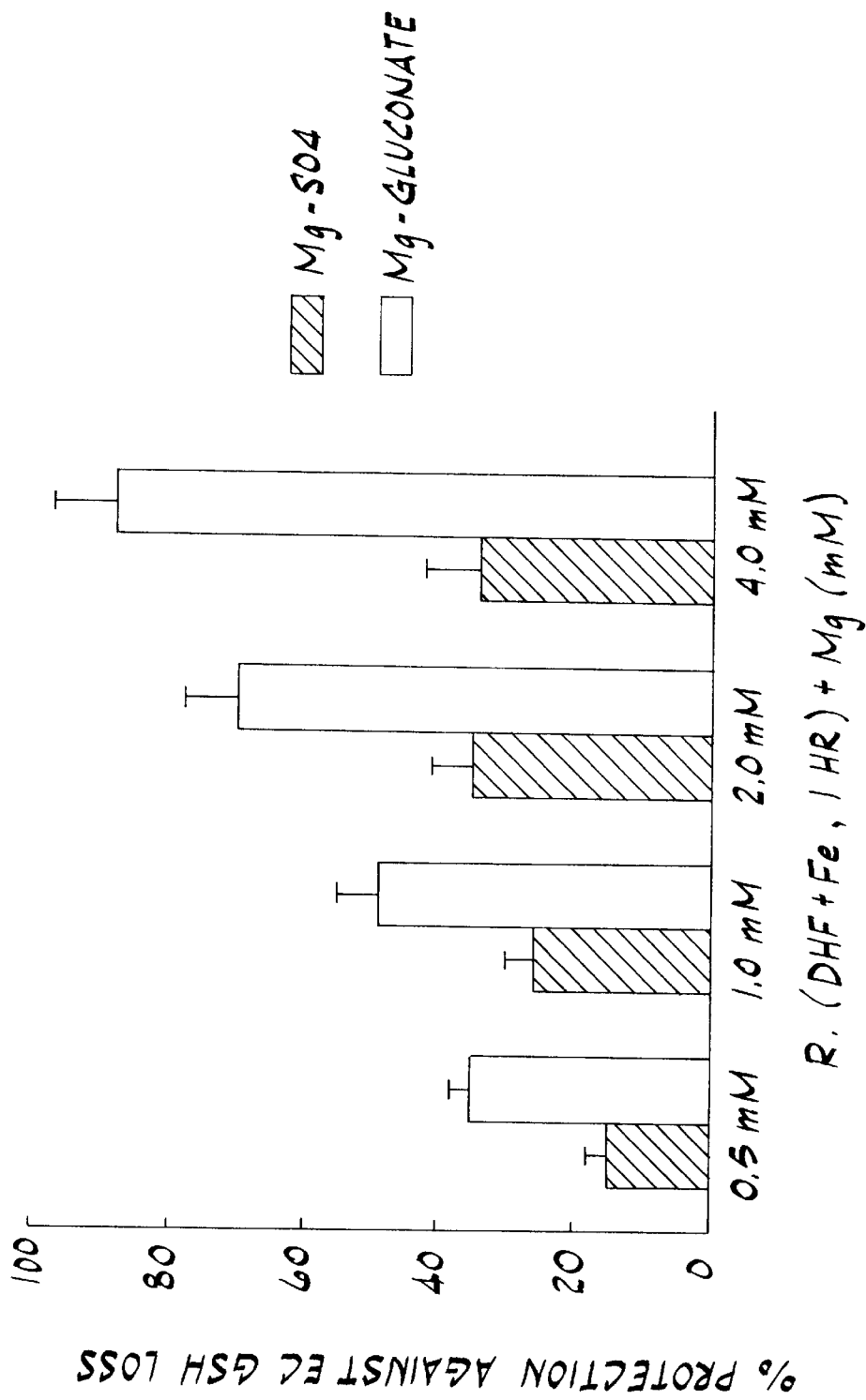

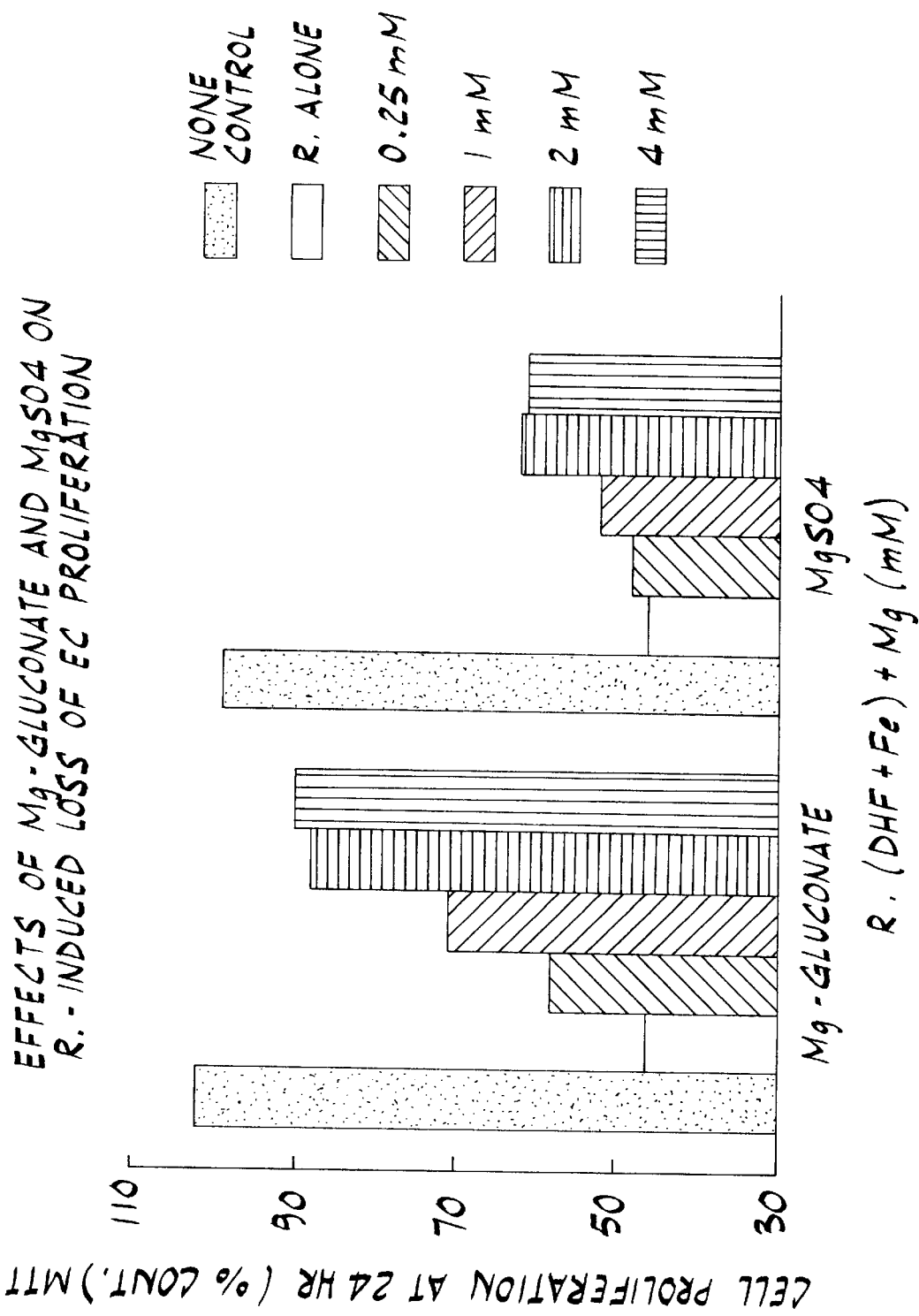

# METHODS AND COMPOSITIONS FOR THE PREVENTION AND TREATMENT OF DIABETES MELLITUS

The present application is a Continuation-in-Part of application Ser. No. 08/588,564 filed Jan. 18, 1996, which is incorporated by reference herein in its entirety.

INTRODUCTION

The present invention relates to methods and compositions for the prevention and treatment of diabetes mellitus. The methods and compositions of the invention, especially suitable for parenteral or enteral administration, prevent or inhibit retinopathy, altered glucose disposition, hypertension, abnormal platelet activity, and other problems encountered in diabetic patients.

BACKGROUND OF THE INVENTION

Diabetes Mellitus

Diabetes mellitus is characterized by a broad array of physiologic and anatomic abnormalities, for example, altered glucose disposition, hypertension, retinopathy, abnormal platelet activity, aberrations involving large, medium and small sized vessels, and other problems encountered in diabetic patients. Diabetics are generally divided into two categories. Patients who depend on insulin for the prevention of ketoacidosis have insulin-dependent diabetes mellitus (IDDM) or type 1 diabetes. Diabetics who do not depend on insulin to avoid ketoacidosis have non-insulin-dependent diabetes mellitus (NIDDM) or type 2 diabetes.

Diabetes is classified into two categories: primary and secondary. Primary diabetes includes: 1) Insulin-dependent diabetes mellitus (IDDM, Type 1), 2) Non-insulin-dependent diabetes mellitus (NIDDM, Type 2) including a) Nonobese NIDDM, b) Obese NIDDM and c) Maturity-onset diabetes of the young. Primary diabetes implies that no associated disease is present, while in the secondary diabetes some other identifiable condition causes or allows a diabetic syndrome to develop, for example, 1) Pancreatic disease, 2) Hormonal abnormalities, 3) Drug or chemical induced, 4) Insulin receptor abnormalities, 5) Genetic syndromes and 6) Others.

Insulin dependence in this classification is not equivalent to insulin therapy, but means that the patient is at risk for ketoacidosis in the absence of insulin. It has been suggested that the terms insulin-dependent and non-insulin-dependent describe physiologic states (ketoacidosis-prone and ketoacidosis-resistant, respectively), while the terms Type 1 and Type 2 refer to pathogenetic mechanisms (immune-mediated and non-immune-mediated, respectively). Using this classification, three major forms of primary diabetes are recognized: (1) type 1 insulin-dependent diabetes, (2) type 1 non-insulin-dependent diabetes, and (3) type 2 non-insulin-dependent diabetes.

Secondary forms of diabetes encompass a host of conditions such as pancreatic disease, hormonal abnormalities, genetic syndromes, and others.

Insulin-dependent diabetes mellitus often develops in childhood or adolescence while the onset of NIDDM generally occurs in middle or late life. Patients with NIDDM are usually overweight and constitute 90 to 95 percent of all diabetics. IDDM results from the destruction of beta cells by an autoimmune process that may be precipitated by a viral infection. NIDDM is characterized by a gradual decline in beta cell function and varying degrees of peripheral resistance to insulin. The annual incidence of IDDM ranges from 10 cases per 100,000 persons for nonwhite males to 16 cases per 100,000 persons for white males. LaPorte, R. E. et al., 1981, *Diabetes* 30: 279. The prevalence of NIDDM increases with age, especially after age 45 and is higher among blacks than whites and certain populations such as Asian Indians living in South Africa and England. Malter, H. M. et al., 1985, *Br. Med. J.* 291: 1081. Gestational diabetes occurs in 2.4 percent of all pregnancies in the United States annually. Freinkel, N. et al., 1985, *N. Engl. J. Med.* 313: 96. Pregnancy is also a state of insulin resistance. This insulin resistance is exacerbated in gestational diabetes which may predispose patients to the various hypertensive syndromes of pregnancy associated with Type 2 NIDDM. Bardicef, M. et al., 1995, *Am. J. Gynecol.* 172: 1009–1013.

Current therapies for IDDM include insulin therapy, and for NIDDM will include dietary modification in a patient who is overweight and hypoglycemic agents, e.g., tolbutamide, chlorpropamide, acetohexamide, tolazamide, glipizide and glyburide, all of which act by stimulating the release of insulin from the beta cells.

Magnesium

Magnesium is an important element for health and disease. It is the fourth most abundant cation in the human body and is the second most abundant intracellular cation. Elin, R. J., 1987, *Clin. Chem.* 33: 1965–1970. Magnesium is a cofactor for approximately 300 enzymes and is essential for energy metabolism and for protein and nucleic acid synthesis. Magnesium deficiency may result secondary to a number of factors including decreased intake or increased gastrointestinal or renal loss of magnesium, drug therapy, and alterations in magnesium distribution. Hypomagnesemia is generally defined as a serum magnesium concentration of less than 1.5 mEq/l. The signs and symptoms of hypomagnesemia include arrhythmias, electrocardiographic changes, hypertension, depression, delirium, agitation, tetany, leg cramps, tremors, ataxia, weakness, confusion and convulsions. The ideal intake of magnesium for an adult is 15 to 20 mmol/d (350 to 450 mg/d). Magnesium is absorbed primarily in the jejunum and ileum, and healthy persons absorb about 30 to 40 percent of ingested magnesium. The majority of adults have a dietary intake of magnesium less than the recommended dietary allowance (RDA) in the range of 43.3 to 93.0 percent of RDA. Pao, E. M., Micke, S. J. 1981, *Food Technol.* 35: 58–69. Hyperglycemia appears to induce magnesium depletion both directly via osmotic diuresis and indirectly by its effect on vitamins, ions and proteins. Yajnik, C. S. et al., 1984, *Br. Med. J.* 288: 1032–1034.

SUMMARY OF THE INVENTION

The present invention relates to methods and compositions for the prevention and treatment of diabetes mellitus using an effective amount of magnesium gluconate. As used herein, diabetes mellitus includes insulin-dependent diabetes mellitus (IDDM) and non-insulin-dependent diabetes mellitus (NIDDM).

The present invention also contemplates the prevention and treatment of the symptoms of diabetes mellitus using an effective amount of magnesium gluconate along with conventional therapy for diabetes mellitus.

The present invention also provides a method for treating and/or preventing hypertension and cardiovascular disease in diabetic subjects by providing a therapeutically effective amount of magnesium gluconate to inhibit production of oxygen free radicals, reduce platelet aggregation and reduce triglyceride concentrations.

The present invention also provides a method for treating and/or preventing diabetic retinopathy and gangrene in diabetic subjects using a therapeutically effective amount of magnesium gluconate.

The present invention also provides a method for treating and/or preventing gestational diabetes in pregnancy using a therapeutically effective amount of magnesium gluconate.

DESCRIPTION OF THE FIGURES

FIG. 1. Effects of magnesium salts on free radical mediated membrane lipid peroxidation.

FIG. 2. Effect of magnesium salts on site-specific $OH^+$-mediated deoxyribose oxidation.

FIG. 3. Effect of magnesium salts on R'.-induced loss of BA-endothelial cell glutathione.

FIG. 4. Effect of magnesium salts on R'.-induced loss of endothelial cell proliferation.

DETAILED DESCRIPTION OF THE INVENTION

The present invention relates to methods and compositions for the prevention and treatment of diabetes mellitus such as insulin-dependent diabetes mellitus and/or non-insulin-dependent diabetes mellitus.

The present invention also provides a method for treating and/or preventing hypertension and cardiovascular disease in diabetic subjects.

The invention further provides a method for reducing platelet aggregation, reducing triglyceride concentrations and inhibiting production of oxygen free radicals.

The invention also provides a method for treating and/or preventing diabetic retinopathy in a diabetic subject.

The present invention is also directed to a method for the prevention and treatment of diabetes mellitus using an effective amount of magnesium gluconate along with conventional therapy for diabetes mellitus.

The present invention further relates to methods and compositions containing magnesium gluconate in combination with antioxidants such as vitamin E, selenium, glutathione, glutathione isopropyl ester, or N-acetylcysteine, for use in the prevention and/or treatment of diabetes mellitus.

"Conventional therapy for diabetes mellitus" used herein, includes diet therapy and insulin therapy. For diet therapy, an estimate is made of the total energy intake needed per day based on ideal body weight (determined from insurance tables). A decision is then made regarding carbohydrate, fat and protein content, and an appropriate diet is constructed from the exchange system provided by the American Dietetic Association. Caloric recommendations from the Food and Nutrition Board for adults carrying out average activity decrease with and range from 175 kJ/kg of body weight (42 kcal/kg) in 18-year old men to 145 kJ/kg (33 kcal/kg) for 75-year old women. Intakes slightly less than recommended are usually preferable; 150-kJ/kg (36 kcal/kg) for men and 140 kJ/kg (34 kcal/kg) for women are reasonable values in most subjects, but upward or downward adjustments may be necessary to achieve desired weight.

Insulin is required for treatment of all patients with insulin-dependent diabetes mellitus and many patients with non-insulin-dependent diabetes. No single standard exists for patterns of administration of insulin and treatment plans vary and may be selected from one of three treatment regimens: conventional, multiple subcutaneous injections, or continuous subcutaneous insulin infusion.

Conventional insulin therapy involves the administration of one or two injections a day of intermediate-activity insulin such as zinc insulin or isophane insulin with or without the addition of small amounts of regular insulin.

The multiple subcutaneous insulin injection technique involves administration of intermediate- or long-acting insulin in the evening as a single dose together with regular insulin prior to each meal. Home glucose monitoring by the patient is necessary if the goal is the return of the plasma glucose level to normal.

Continuous subcutaneous insulin infusion involves use of a small battery-driven pump that delivers insulin subcutaneously into the abdominal wall, usually through a 27-gauge butterfly needle. Insulin is delivered at a basal rate continuously throughout the day, with increased rates programmed prior to meals.

Non-insulin-dependent diabetes that cannot be controlled by dietary management often responds to sulfonylureas. Sulfonylureas act primarily by stimulating release of insulin from the beta cell.

"Oxygen free radical" used herein, refers to a free radical molecule with an odd, unpaired electron which makes the molecule unstable and highly reactive. Tribble, D. L. et al. 1987, *Hepatology* 7: 377–386. Small amounts of these molecules are produced endogenously by the mitochondrial electron transport system and the endoplasmic reticulum in microsomes and peroxisomes. Oxygen free radicals, the superoxide anion ($O_2^-$) the hydroxyl radical (°OH), and their intermediary, hydrogen peroxide ($H_2O_2$) are believed to be generated in vascular complications associated with diabetes mellitus, e.g., platelet aggregation. The free radicals interact with other cellular constituents such as deoxyribonucleic acid (DNA) and lipids and lead to subsequent formation of multiple degradation products. Lipid peroxidation forms lipid peroxides and aldehydes that interact with protein sulfhydryl groups and thereby perpetuate cellular damage. Del Maestro, R. F., 1980, *Acta. Physiol. Scand.* 492 (Suppl.): 153–168.

Normally, protective mechanisms are present in the cell to prevent damage by free radicals. For example, the primary mechanism of clearance of $O_2^-$ from biologic systems is superoxide dismutase, which catalyses the dismutation of $O_2^-$ to $H_2O_2$ and $O_2$. The cytoplasmic enzymes glutathione peroxidase and catalase provide the fmal detoxification steps with the reduction of $H_2O_2$ to $O_2^-$. Glutathione peroxidase seems to be a more active enzyme than catalase in protecting cells such as myocardial cells or endothelial cells from $H_2O_2$-mediated damage. Fridovich, I., 1983, *Annu. Rev. Pharmacol. Toxicol.* 23: 239–257; Fantone, J. C., et al., 1982, *Am. J. Pathol.* 107: 395–418.

The present invention provides a method comprising administering to a subject having diabetes mellitus a composition of magnesium gluconate in sufficient amounts to inhibit oxygen free radical production and lipid peroxidation.

In different embodiments of the invention, the composition of the invention is administered enterally or parenterally in the prevention or treatment of diabetes mellitus.

The compositions of the invention comprise tablets, aqueous solutions and nutrient preparations containing magnesium gluconate in an amount sufficient to inhibit oxygen free radical production and lipid peroxidation in various vascular and membrane tissues.

Administration of magnesium gluconate results in cellular resistance to oxygen free radical stress and free radical production, for example lipid peroxides and prostaglandins.

Glucose metabolism is altered by prostaglandins which participate with insulin in favoring the uptake of glucose into the skeletal muscle. Dietze G., et al., 1979, *Adv. Exper. Med. Biol.* 120A: 511–520. Thus diabetes mellitus is affected by the quantity and types of prostaglandins present. The insulin response to glucose in diabetes mellitus is improved by the administration of inhibitors of prostaglandin production. The preferred composition of the invention contains magnesium gluconate, desirably at a concentration of about 0.1 mM to about 1.5M.

Magnesium is an important metallo coenzyme for many enzyme reactions. In the method of the present invention, magnesium gluconate inhibits the production of free radicals, reduces cellular damage due to oxidative stress, reduces lipid peroxidation, reduces glutathione loss and increases the sensitivity of cells to insulin.

Metabolic Complications in Diabetes

The association between diabetes mellitus, diabetic complications and hypomagnesemia has been suggested. American Diabetes Association, 1992, *Diabetes Care* 15: 1065–1067. Acute metabolic complications observed in diabetic subjects include hypoglycemia and diabetic ketoacidosis. Late complications of diabetes that may cause morbidity and premature mortality include circulatory abnormalities, retinopathy, diabetic nephropathy, diabetic neuropathy and diabetic foot ulcers.

Hypomagnesemia was noted in subjects having: diabetic ketoacidoses (Moles, K. W. and McMullen, J. K, 1982, *Br. Med. J.* 285: 262), diabetic retinopathy (McNair, P. et al., 1978, *Diabetes* 27: 1075–1077), hypertension (Resnick, L. M. et al., 1987, *Proc. Natl. Acad. Sci. USA* 84: 7663–7667), abnormal platelet activity (Altura, B. M. and Altura, B. T., 1985, *Magnesium* 4: 226–244), lipidemias (Rayssiguier, Y. and Gueux, E., 1986, *J. Am. Coll. Nutr.* 5: 507–519) and gestational diabetes (Bardicef, M. et al., 1995, *Am. J. Gynecol.* 172: 1009–1013). The exact nature of the relationship between diabetes mellitus and magnesium remains to be explained. However, the compositions and methods of the present invention are especially suited for use in the treatment and prevention of diabetes mellitus by virtue of their enhanced properties as antioxidants compared with other magnesium salts as described infra, in Section 6 and by virtue of having minimal purgative action on the gut.

Pharmaceutical Preparations and Methods of Administration

Magnesium gluconate compositions for use in accordance with the present invention are formulated by mixing magnesium gluconate into an aqueous solution or by mixing a suitable magnesium salt, for example, magnesium carbonate, with glucono-delta-lactone or magnesium carbonate with glucono-delta lactone and/or citric acid. Desirably, the following concentrations are utilized: magnesium carbonate in the range of 2 mg per liter to 44 g per liter; citric acid in the range of 2.3 mg. per liter to 46.2 g per liter; and glucono-delta-lactone in the range of 6 mg per liter to an amount capable of reacting with up to 44 g per liter of magnesium carbonate and up to 46.2 g per liter of citric acid, being not greater than 130 g per liter. There results an aqueous solution of magnesium gluconate or magnesium gluconate/citrate, i.e., a solution containing magnesium gluconate and magnesium citrate that exerts unexpected and stronger antioxidant, antiperoxidative and cytoprotective effects than other magnesium salts as described in Section 7.0 below. In addition, magnesium gluconate is included in a nutritional formula or may be in the form of tablets, capsules and powdered or granular preparations which are reconstituted to provide an aqueous composition.

Aqueous magnesium gluconate composition of the invention comprise formulations suitable for enteral and parenteral administration.

The identified compositions that prevent and/or treat diabetes mellitus can be administered to a patient at therapeutically effective doses. A therapeutically effective dose refers to that amount of the magnesium compound sufficient to result in the amelioration of symptoms of diabetes mellitus. Similarly, a therapeutically effective dose refers to that amount of the antioxidants, including but not limited to, Vitamin E, selenium, glutathione, glutathione isopropyl ester or N-acetylcysteine, sufficient to result in the amelioration of symptoms of diabetes mellitus.

Toxicity and therapeutic efficacy of the magnesium compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% in the population). The dose ratio between toxic and therapeutic effects is the therapeutic index and it can be expressed as the ratio $LD_{50}/ED_{50}$. Compounds which exhibit large therapeutic indices are preferred. The data obtained from the cell culture assays and animal studies can be used in formulating a range of dosages for use in humans.

Formulations

Magnesium gluconate compositions for use in accordance with the present invention are formulated by mixing magnesium gluconate into an aqueous solution or by mixing a suitable magnesium salt, for example, magnesium carbonate, with glucono-delta-lactone or magnesium carbonate with glucono-delta lactone and/or citric acid. Pharmaceutical compositions for use in accordance with the present invention can be formulated by conventional means in aqueous form or by using one or more physiologically acceptable carriers, excipients or buffers.

Thus, the compounds and their physiologically acceptable salts and solvates can be formulated for administration by insufflation (either through the mouth or the nose) or oral, buccal, parenteral or rectal administration.

For oral administration, the pharmaceutical compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate or talc); disintegrants (e.g., potato starch or sodium starch glycolate); or wetting agents (e.g., sodium lauryl sulphate). The tablets can be coated by methods well known in the art. Liquid preparations for oral administration can take the form of, for example, aqueous solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydrobenzoates or sorbic acid). The preparations can also contain buffer salts, flavoring, coloring and sweetening agents as appropriate. The preparations can also take the form of nutritional formulas.

Preparations for oral administration can be formulated to give controlled release of the active compound.

For buccal administration the compositions can take the form of tablets or lozenges formulated in the conventional manner.

The compounds can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form, tablets or capsules for constitution with a suitable vehicle, e.g., sterile pyrogen-free water, before use.

The compounds can also be formulated in rectal compositions such as suppositories or retention enemas, e.g., containing conventional suppository bases such as cocoa butter, other glycerides or carbowax.

In addition to the formulations described previously, the compounds can also be formulated as a depot preparation. Such long acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device which can contain one or more unit dosage forms containing the active ingredient. The pack can for example comprise metal or plastic foil, such as a blister pack. The pack or dispenser device can be accompanied by instructions for administration.

Patient dosages for enteral or parenteral administration range from 10 to 150 mEq of magnesium gluconate per day, commonly 20–50 mEq per day, and typically from 20 to 30 mEq per day. Stated in terms of milligrams of Mg, dosages range from 100 mg per day to 1800 mg per day, commonly 250 mg to 600 mg per day.

Dosage amounts of calcium for enteral administration range from 500 to 1500 mg per day. Dosage amounts of antioxidants for enteral administration range from, for example, for vitamin E: 200 to 1000 I.U. per day. Dosage amount and interval may be adjusted to provide plasma levels which are sufficient to maintain normal metabolism.

EXAMPLE

The antioxidant properties of magnesium gluconate were studied by incubating microsomal membranes prepared from endothelial cells in the presence of 0.25, 0.5, 1.0 and 2.0 mM of magnesium salts including magnesium gluconate, magnesium sulfate and magnesium chloride or sodium gluconate. Membrane malondialdehyde and site specific OH-mediated deoxyribose oxidation were measured according to methods described by Mak, I. T. & Weglicki, W. B., 1994, *Method Enzymol.* 234: 620–630; and Mak, I. T., et al., 1990, *Biochem. Pharm.* 40: 2169–2175. Results demonstrate that magnesium gluconate is more effective than magnesium sulfate or sodium gluconate in inhibiting free radical production (malondialdehyde) (FIG. 1). Magnesium gluconate is also more effective than magnesium chloride or magnesium sulfate in inhibiting free radical mediated deoxyribose oxidation in a dose-related manner. (FIG. 2). These data indicate magnesium gluconate has unexpected and more powerful antioxidant properties than other magnesium salts.

Cultured bovine aortic (BA) endothelial cells were incubated with R. (R.=0.83 mM dihydroxyfumarate+0.025 mM $Fe^{3+}$-ADP) for 50 mins at 37° C. Glutathione (GSH) was then determined by the enzymatic method described by Mak, I. T., et al., 1992, *Cir. Res.* 70: 1099–1103. A loss of 56% of total GSH was observed. When the cells were pretreated for 10 mins with varying amounts of magnesium gluconate or magnesium sulfate before being exposed to R., magnesium gluconate significantly prevented the GSH loss to varying degrees ($p<0.05$). The EC50 was 1.1 mM (FIG. 3).

When endothelial monolayers (about 65% confluent) were incubated with R. for 30 min, the cell survival/proliferation determined by the tetrazolium salt MTT assay (Mak, I. T., et al., 1995, *Biochem. Pharmacol.* 50: 1531–1534), decreased to 38% of control at 24 hr. Pretreatment with magnesium gluconate attenuated the loss in cell survival/proliferation (expressed as % of control (cont.)) in a dose-dependent manner compared with the cells pretreated with magnesium sulfate (FIG. 4).

It is important to note that the effects of magnesium sulfate on R.-induced loss of GSH or R.-induced loss of cell survival/proliferation were much lower than those obtained with magnesium gluconate, i.e., magnesium sulfate were approximately 33% as potent as magnesium gluconate (FIGS. 1–4).

EXAMPLE TREATMENT BEGINS FOR DIABETES MELLITUS

The invention is illustrated, by way of protocols for diabetes mellitus in subjects suffering from non-insulin dependent diabetes.

30 mL magnesium gluconate (324 mg Mg)(Magonate®—Fleming and Co., Pharmaceuticals) is given three times daily alone or in combination with diet therapy, insulin therapy or diet therapy+insulin therapy. The magnesium status of each subject (control or patient with diabetes mellitus) in study is evaluated by measuring serum magnesium concentration, erythrocyte magnesium concentrations, leukocyte magnesium concentrations and 24-hour magnesium excretion. The methods employed include use of ion-selective electrodes and nuclear magnetic resonance spectroscopy, as described by Elin, R. J., 1987, *Clin. Chem.* 33: 1965–1970; Deuster, P. A. et al., 1987, *Clin. Chem.* 33: 529–532; and Bardicef, M., et al., 1995, *Am. J. Obstet. Gynecol.* 172: 1009–1013.

The total amount of lipid peroxidation products present in the plasma samples of subjects studied is estimated using the thiobarbituric acid (TBA) method (described in Section 6) to measure by malondialdehyde (MDA) reactive products. The MDA levels are measured prior to and at 4, 8 and 12 weeks after start of magnesium gluconate. The magnesium gluconate compositions of the present invention are useful in the prevention and/or treatment of diabetes mellitus.

The present invention is not to be construed as limited in scope to the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. A method for preventing or treating diabetes mellitus comprising administering to a subject a therapeutically effective amount of magnesium gluconate.

2. A method for preventing or treating diabetes mellitus caused by or related to production of oxygen free radicals in a human subject, the method comprising administering to the human subject an effective amount of magnesium gluconate.

3. The method of claim 2, wherein the magnesium gluconate is present in solution at a concentration within the range of approximately 0.1 mM to about 1.5M.

4. The method of claim 2, wherein the magnesium gluconate is administered enterally.

5. The method of claim 2, wherein the magnesium gluconate is administered parenterally.

6. The method of claim 2, wherein the magnesium gluconate is administered topically.

7. The method of claim 2, wherein the magnesium gluconate is administered rectally.

8. The method of claim 2 further comprising administering an insulin regimen.

9. The method of claim 2 further comprising administering one or more antioxidants selected from the group consisting of vitamin E, selenium, glutathione, glutathione isopropyl ester and N-acetylcysteine.

10. The method of claim 8 further comprising administering one or more antioxidants selected from the group consisting of vitamin E, selenium, glutathione, glutathione isopropyl ester and N-acetylcysteine.

11. A composition suitable for administering to a human subject for the prevention or treatment of diabetes mellitus, said composition consisting essentially of magnesium gluconate and an antioxidant selected from the group consisting of vitamin E, selenium, glutathione, glutathione isopropyl ester and N-acetylcysteine.

12. The composition of claim 11, wherein the magnesium gluconate is in solution at a concentration within the range of from about 0.1 mM to about 1.5M.

13. The composition of claim 11, wherein the concentration of magnesium gluconate is sufficient to treat or prevent symptoms of diabetes mellitus related to production of oxygen free radicals and lipid peroxidation.

* * * * *